United States Patent
He

(10) Patent No.: US 11,318,222 B2
(45) Date of Patent: May 3, 2022

(54) ULTRAVIOLET LAMP

(71) Applicant: FOSHAN COMWIN LIGHT & ELECTRICITY CO., LTD, Guangdong (CN)

(72) Inventor: Zhiming He, Guangdong (CN)

(73) Assignee: FOSHAN COMWIN LIGHT & ELECTRICITY CO., LTD, Guangdong (CN)

(*) Notice: Subject to any disclaimer, the term of this patent is extended or adjusted under 35 U.S.C. 154(b) by 0 days.

(21) Appl. No.: 17/263,641

(22) PCT Filed: Jun. 18, 2019

(86) PCT No.: PCT/CN2019/091662
§ 371 (c)(1),
(2) Date: Jan. 27, 2021

(87) PCT Pub. No.: WO2020/232783
PCT Pub. Date: Nov. 26, 2020

(65) Prior Publication Data
US 2022/0062486 A1    Mar. 3, 2022

(30) Foreign Application Priority Data

May 20, 2019  (CN) .......................... 201910421223.8
May 20, 2019  (CN) .......................... 201910438703.5

(51) Int. Cl.
*A61L 9/20* (2006.01)
*H01J 61/26* (2006.01)
*C02F 1/32* (2006.01)

(52) U.S. Cl.
CPC ................ *A61L 9/20* (2013.01); *C02F 1/325* (2013.01); *H01J 61/26* (2013.01); *A61L 2209/12* (2013.01); *C02F 2201/32* (2013.01)

(58) Field of Classification Search
CPC .................................................... H01J 61/26
See application file for complete search history.

(56) References Cited

U.S. PATENT DOCUMENTS

| 5,274,305 A | 12/1993 | Bouchard |
| 2004/0232846 A1 | 11/2004 | Fischer et al. |
| 2005/0189864 A1 | 9/2005 | Fischer |

FOREIGN PATENT DOCUMENTS

| CN | 1489176 A | 4/2004 |
| CN | 101248511 A | 8/2008 |

(Continued)

OTHER PUBLICATIONS

International Search Report and Written Opinion dated Feb. 12, 2020, for related International Application No. PCT/CN2019/091662; 11 Pages.

(Continued)

*Primary Examiner* — Vip Patel
(74) *Attorney, Agent, or Firm* — Brooks Kushman P.C.

(57) ABSTRACT

An ultraviolet lamp includes a lamp tube and an electrode. A discharge cavity is formed in the lamp tube. A thermistor is disposed on an end socket at a first end of the lamp tube. A receiving groove communicated with the discharge cavity is formed in the end socket and contains amalgam. The thermistor heats the amalgam in the receiving groove in the end socket. The Curie temperature of the thermistor ranges from $[T1+(T2-T1)/5]$ to $[T1+4*(T2-T1)/5]$, wherein T1 and T2 are respectively a minimum operating temperature and a maximum operating temperature of the amalgam in a continuous region where the ultraviolet radiation power is from 90% to 100% when the input power of the ultraviolet lamp is 100%.

6 Claims, 3 Drawing Sheets

(56) References Cited

FOREIGN PATENT DOCUMENTS

| | | |
|---|---|---|
| CN | 101496133 A | 7/2009 |
| CN | 105470100 A | 4/2016 |
| CN | 105582570 A | 5/2016 |
| CN | 107007853 A | 8/2017 |

OTHER PUBLICATIONS

Chinese Office Action dated Dec. 26, 2019, for related Chinese Appln. No. 201910421223.8; 16 Pages.
Chinese Office Action dated Mar. 27, 2020, for related Chinese Appln. No. 201910421223.8; 8 Pages.
Chinese Notice of Allowance, for related Chinese Appln. No. 201910421223.8; 3 Pages.

ULTRAVIOLET LAMP

CROSS-REFERENCE TO RELATED APPLICATIONS

This application is a national phase application of international application Serial No. PCT/CN2019/091662 filed Jun. 18, 2019, now pending, which, in turn, claims the benefit of Chinese application Serial No. 201910421223.8 filed May 20, 2019 and Chinese application Serial No. 201910438703.5 filed May 20, 2019, the disclosures of which are hereby incorporated in their entirety by reference herein.

TECHNICAL FIELD

The invention relates to the field of ultraviolet sterilization of water and air, in particular to a low-pressure and high-intensity ultraviolet lamp with enhanced environmental adaptability

BACKGROUND

At present, wastewater, reclaimed water, tap water and drinking water are generally sterilized by means of ultraviolet lamps, that is, ultraviolet light is used to kill various microorganisms. In addition, existing biochemical degradation, ozone degradation, hydrogen peroxide degradation, Fenton advanced oxidation and electrochemical processes for treating industrial wastewater, reclaimed water and drinking water with out-of-limit COD and trace organic substances have the defect of being unable to degrade all organic substances or high in degradation cost. As a novel organic substance degradation method, hydroxyl radicals generated under the synergistic effect of ultraviolet light and ozone, hydrogen peroxide, or ozone and hydrogen peroxide can be used to oxidize various COD and trace organic substances, so ultraviolet advanced oxidization is also an important method for degrading organic substances for water treatment.

In the prior art, there have already been ultraviolent lamps used for sterilizing water or degrading organic substances. The operating principle of such ultraviolet lamps is as follows: electrodes used for discharging are disposed at two ends of a lamp tube filled with mercury vapor; when the electrodes discharge to the mercury vapor, electrons impact with mercury atoms to generate ultraviolet photons, that is, ultraviolet light is generated. At present, in the technical field of large-scale water purification and sterilization, low-pressure and high-intensity ultraviolet lamps are typically used as sterilization apparatuses to improve the ultraviolet sterilization efficiency.

It is worth mentioning that that when ultraviolet lamps are used for water purification, working parameters such as the water flow rate and the ultraviolet transmittance of water in the purification area may change during use, so the ultraviolet doses required for killing microorganisms under different working parameters are also different. For example, in case of a low water flow rate or a high ultraviolet transmittance of water, the ultraviolet dose required is small, and the power of the ultraviolet lamps, namely the ultraviolet radiation power, should be reduced to reduce energy consumption. Similarly, during the ultraviolet advanced oxidization process, when the ultraviolet transmittance of water increases or the concentration of ozone/hydrogen peroxide decreases, the power of the ultraviolet lamps, namely the ultraviolet radiation power, should be reduced to optimize the reaction efficiency and reduce energy consumption.

Similar problems exist in the fields of ultraviolet sterilization and purification of an air supply system in the breeding industry, deodorization and sterilization of an exhaust system in the breeding industry with 185 nm and 253.7 nm double-waveband ultraviolet light, and infectious disease prevention and control in public places. The large temperature difference and the variation of the wind speed in winter and summer seriously affect the radiation efficiency of the ultraviolet lamps.

In addition, another indicator for evaluating the performance of the ultraviolet lamps is the ultraviolet radiation efficiency. According to the operating principle of the ultraviolet lamps, to maintain the ultraviolet radiation efficiency of traditional low-pressure ultraviolet lamps at a high level, the mercury vapor pressure in the lamps should be close to the optimal mercury vapor pressure matching the working condition, which may otherwise drastically reduce the ultraviolet radiation efficiency of the ultraviolet lamps. However, due to a larger current density and a larger number of electrons of low-pressure and high-intensity ultraviolet lamp tubes, the corresponding optimal mercury vapor pressure is a bit higher than that of the low-pressure ultraviolet lamps, so compared with other traditional low-pressure ultraviolet lamps, the ultraviolet radiation characteristic of the low-pressure and high-intensity ultraviolet lamps is more sensitive to the variation of the mercury vapor pressure, and under a constant variation amplitude of the mercury vapor pressure, the ultraviolet radiation power or the ultraviolet radiation efficiency of the low-pressure and high-intensity ultraviolet lamps will change to a greater extent. Thus, there is an urgent demand at present for a novel ultraviolet lamp design to solve the problem of fluctuations of the ultraviolet radiation power of the low-pressure and high-intensity ultraviolet lamps to ensure that the low-pressure and high-intensity ultraviolet lamps can better adapt to the fluctuations of environmental factors such as the temperature and the flow rate in the working area.

SUMMARY

To overcome the above-mentioned technical defects, the objective of the invention is to provide a low-cost ultraviolet lamp that can maintain high ultraviolet radiation efficiency under a wide variation range of environmental factors such as the temperature, the flow rate and power regulation.

The invention discloses an ultraviolet lamp, comprising a lamp tube and an electrode, wherein a discharge cavity is formed in the lamp tube, a thermistor is disposed on an end socket at a first end of the lamp tube, a receiving groove communicated with the discharge cavity is formed in the end socket, amalgam is stored in the receiving groove, and the thermistor heats the amalgam in the receiving groove in the end socket.

Preferably, the receiving groove is at least one of a flat groove, an ellipsoidal groove, a conical groove, a spherical groove and a tubular groove.

Preferably, the Curie temperature of the thermistor ranges from $[T1+(T2-T1)/5]$ to $[T1+4*(T2-T1)/5]$.

Preferably, the Curie temperature of the thermistor ranges from 90° C. to 135° C., and the current density of the ultraviolet lamp is greater than 0.13 ampere per square centimeter.

Preferably, at least one terminal of a thermistor lead wire is connected to one terminal of electrode lead wires.

Preferably, two terminals of the thermistor lead wire are connected to one terminal of the electrode leads wires at two ends respectively.

Preferably, the thermistor and the receiving groove are wrapped with at least one of a heat-conducting silica gel and a silica gel sheath.

Preferably, the receiving groove contacts with the thermistor directly, or indirectly through a heat-conducting material.

Preferably, the ultraviolet lamp further comprises an outer sleeve disposed around the lamp tube and spaced from the lamp tube, wherein the distance between an inner wall of the outer sleeve and an outer wall of the lamp tube is 1.0 mm-5.0 mm, and the lamp tube and the outer sleeve are connected in a non-sealed manner.

Preferably, the ultraviolet lamp further comprises an outer sleeve disposed around the lamp tube and spaced from the lamp tube, wherein the distance between an inner wall of the outer sleeve and an outer wall of the lamp tube is 1.0 mm-5.0 mm, the lamp tube and the outer sleeve are connected in a sealed manner, at least one of an inert gas and nitrogen is filled between the lamp tube and the outer sleeve, both the lamp tube and the outer sleeve are made of quartz pervious to 185 nm and 253.7 nm ultraviolet light, and the lamp tube and the outer sleeve are integrated and are able to output the 185 nm and 253.7 nm ultraviolet light Preferably, the amalgam comprises bismuth, indium, tin and mercury, wherein the proportion of the mercury is 2.0/6-2.5%. Compared with the prior art, the invention adopting the above technical solution has the following beneficial effects:

1. The ultraviolet lamp can maintain high ultraviolet radiation efficiency within a wide variation range of environmental factors such as the temperature, flow rate and power regulation;

2. The structure of existing ultraviolet lamps does not need to be drastically improved, and the cost is low.

Figure 1:
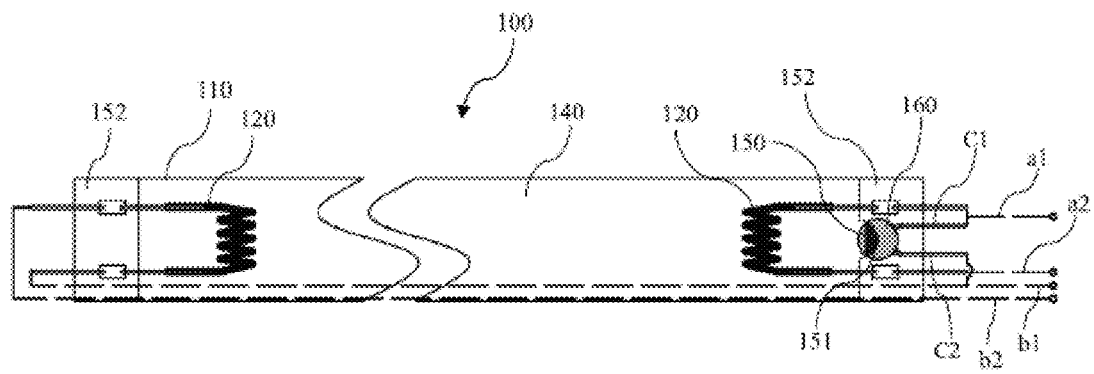
FIG. 1 is an overall structural view of an ultraviolet lamp of the invention.

REFERENCE SIGNS 100, ultraviolet lamp; 110, lamp tube; 120, electrode; 130, ballast; 140, discharge cavity; 150, amalgam; 160, thermistor; 170, silica gel sheath; 180, outer sleeve; 151, receiving groove; 151A, flat groove; 151B, spherical groove; 151C, tubular groove; 151D, conical groove; 151E, ellipsoidal groove; 152, end socket; a1, a2, b1, b2, electrode lead wire; C1, C2, thermistor lead wire.

DETAILED DESCRIPTION

It should be noted that the embodiments of the application and the characteristics in the embodiments can be combined without causing any contradictions. The invention will be described in detail below with reference to the accompanying drawings and embodiments.

To make those skilled in the art have a better understanding of the technical solutions of the invention, the technical solutions of the embodiments of the invention will be clearly and completely described below in conjunction with the drawings of the embodiments of the invention. Obviously, the embodiments in the following description are merely illustrative ones, and are not all possible ones of the invention. All other embodiments obtained by those ordinarily skilled in the art on the basis of the following ones without creative labor should also fall within the protection scope of the invention.

It should be noted that terms such as "first" and "second" in the specification, claims and accompanying drawings of the invention are used to distinguish similar objects, and do not necessarily indicate a specific sequence or a precedence order. It should be understood that data referred to can be exchanged in an appropriate case to allow the embodiments described below to be implemented in other sequences expect those illustrated or described herein. In addition, terms such as "comprises" and "provided with" and any transformations thereof refer to exclusive inclusions.

To solve the problem of fluctuations of the ultraviolet radiation power of low-pressure and high-intensity ultraviolet lamps, a low-pressure and high-intensity ultraviolet lamp in the invention uses amalgam instead of liquid mercury to control the mercury vapor pressure therein to guarantee high ultraviolet radiation efficiency of the low-pressure and high-intensity ultraviolet lamp. It should be noted that the mercury vapor pressure generated by the amalgam also varies along with the variation of the environmental temperature and the current and power of the lamp.

After a long-term study, the inventor finds that when the temperature variation of the amalgam meets $\Delta T=30\text{-}40°$ C., the mercury vapor pressure in the lamp can be controlled to be close to a specific mercury vapor pressure, such as 1.0-1.7 Pa. In the invention, the low-pressure and high-intensity ultraviolet lamp is described in case of being applied to the field of water sterilization by way of example. In actual application, the water temperature fluctuation $\Delta T$ in different places or regions is generally about 30° C., for example, the water temperature range in the northern region in China is 3-30° C., the water temperature range in the central region in China is 5-35° C., and the water temperature range in the southern region of China is 8-40° C. The temperature of the amalgam in the lamp will vary accordingly with the variation of the water temperature.

On this basis, the variation range of the temperature of the amalgam is influenced by a heat conduction difference caused by the dimensions of a sleeve and a lamp tube of the ultraviolet lamp and a difference of the design temperature of the tube wall of the lamp, so the calculation formula of the temperature variation of the amalgam is $\Delta T*k$, wherein $\Delta T$ is the variation amplitude of the water temperature, and k is a specific coefficient and is generally from 0.8 to 1.2. For example, if the regulation range of the current or power of the lamp is 60-100%, the variation range of the temperature of the amalgam will be about 25° C., and the total temperature variation ΔT of the amalgam under the variation of the water temperature and the variation of the lamp power is about 55° C. (namely, 30° C.+25° C.). For example, in an extreme case where the water temperature is 5° C., the power of the ultraviolet lamp is 60% of the full load and the temperature of the amalgam is 85° C., or in another extreme case where the water temperature is 35° C., the power of the ultraviolet lamp is 100% of the full load and the temperature of the amalgam is 140° C., the temperature variation of the amalgam will reach 55° C. However, it is hard for existing amalgam to control the mercury vapor pressure in the lamp to be close to the specific optimal mercury vapor pressure within these temperature ranges.

In view of this, a major improvement of the invention is to control the temperature of the amalgam to stabilize the temperature range of the amalgam. On this basis, the invention provides an implementation where a small heating element (such as a heating wire), a temperature sensor and a control circuit are additionally arranged in the ultraviolet lamp to maintain the temperature of the amalgam within a specific range.

By adoption of the technical means in this solution, the issue of temperature control of the amalgam can be settled to some extent, but the implementation cost is high; in addition, to make the lamp compatible with other equipment, two lamp holders are needed, and multiple components should be additionally arranged in the lamp holders, which makes the structure more complicated; and, if the control circuit is exposed to a high temperature environment of 80-100° C. for a long time, the failure rate of the control circuit will be greatly increased.

In addition, if the regulation range of the current or power of the lamp is expanded to 30-100% of the full load, under the condition where the temperature variation ΔT of the amalgam caused by the variation of the water temperature and the variation of the power is greater than or equal to 65° C., a heating temperature controller may fail to accurately control the temperature under the influence of heat conduction. So, not only the temperature of the amalgam should be controlled, but also an appropriate amalgam proportion should be selected, and the design parameters of the lamp need to be coordinately adjusted, which are technically blank in the art.

Figure 2:
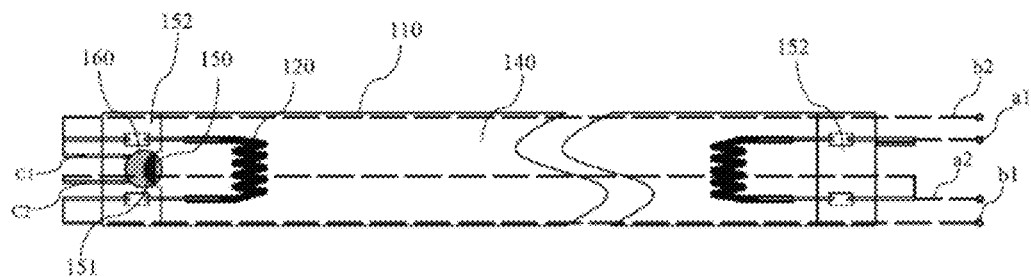
FIG. 2 is an overall structural view of the ultraviolet lamp of the invention.
Figure 3:
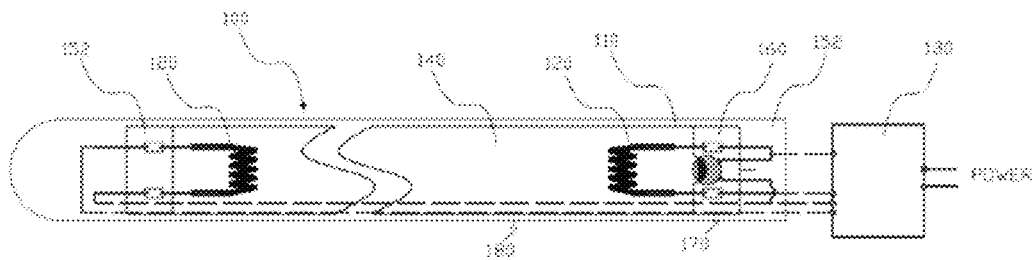
FIG. 3 is an overall structural view of an ultraviolet lamp provided with an enclosed outer sleeve of the invention.
Figure 4:
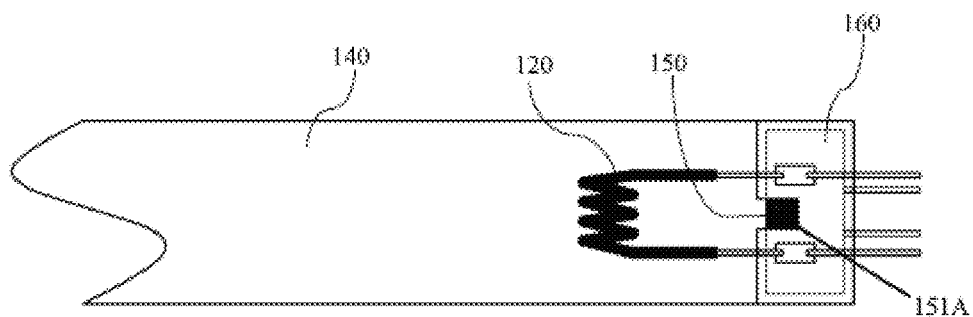
FIG. 4 is a structural view of a flat groove of the ultraviolet lamp of the invention.
Figure 5:
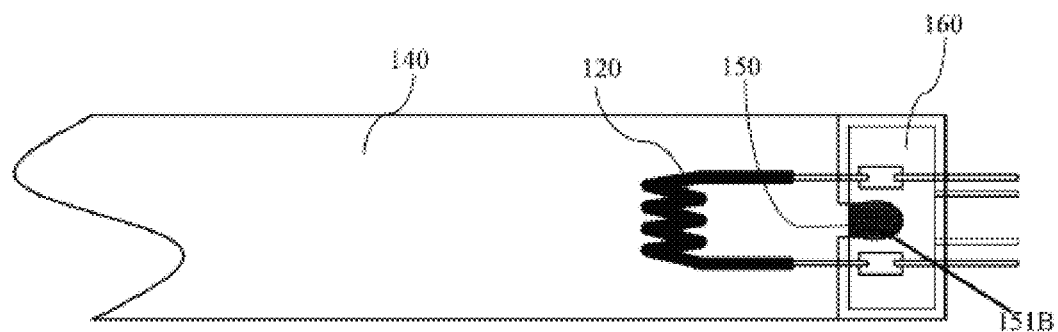
FIG. 5 is a structural view of a spherical groove of the ultraviolet lamp of the invention.
Figure 6:
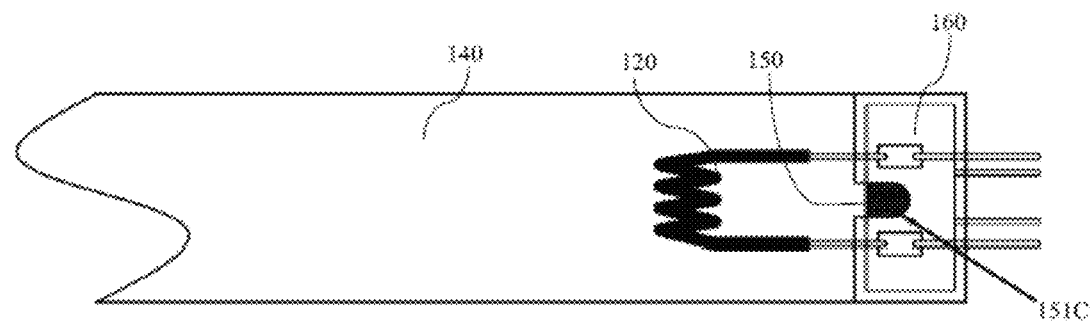
FIG. 6 is a structural view of a tubular groove of the ultraviolet lamp of the invention.
Figure 7:
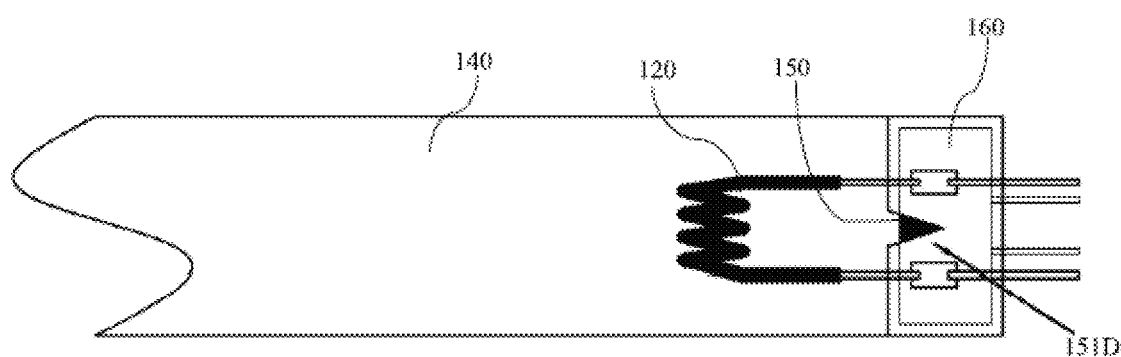
FIG. 7 is a structural view of a conical groove of the ultraviolet lamp of the invention.
Figure 8:
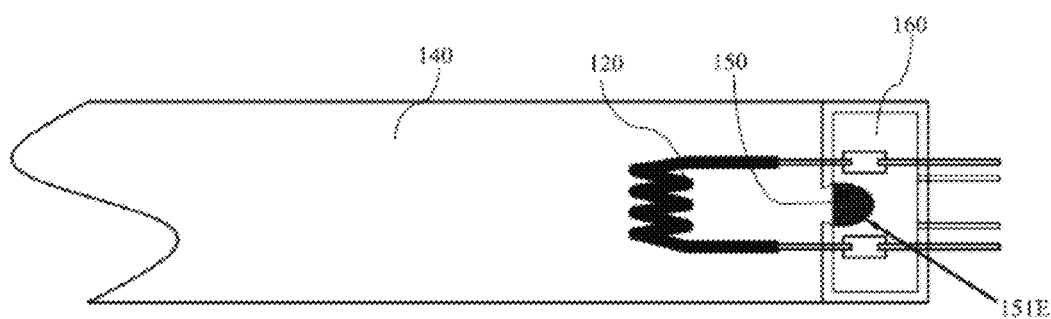
FIG. 8 is a structural view of an ellipsoidal groove of the ultraviolet lamp of the invention.
Figure 9:
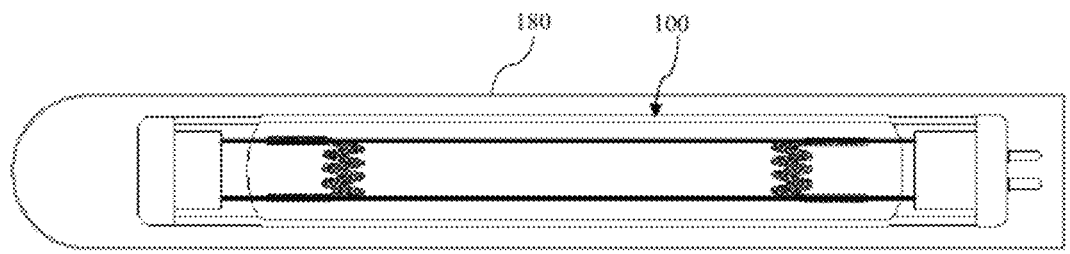
FIG. 9 is a structural view of an ultraviolet lamp not provided with an enclosed outer sleeve of the invention.

For the sake of a preferred implementation, as shown in FIG. 1 to FIG. 9, the invention provides the following preferred embodiment. Wherein, the overall structure of the ultraviolet lamp is illustrated in FIG. 1 to FIG. 3. The ultraviolet lamp 100 is used for water sterilization by radiating ultraviolet light to kill microorganisms in water or promote organic substances in water to be degraded. In this embodiment, the ultraviolet lamp 100 is a low-pressure and high-intensity ultraviolet lamp, that is, the pressure in the lamp is low, and the current density of the lamp during operation is preferably greater than 0.13 ampere per square centimeter. The ultraviolet lamp 100 comprises:

A Lamp Tube 110

Wherein, the lamp tube 110, as a major structure of the ultraviolet lamp 100, is made of light-pervious silica glass, the interior of the lamp tube 110 is enclosed, and a discharge cavity 140 is formed in the lamp tube 110. In a working state, the discharge cavity 140 is filled with mercury vapor given off by amalgam. End sockets 152 are arranged at two ends of the lamp tube 110, and electronic components, such as electrodes 120 and a thermistor 160 mentioned below, can be connected into the end sockets 152 in a sealed state.

Electrodes 120

Wherein, the electrodes 120 are separately and oppositely arranged at the two ends of the lamp tube 110 to discharge.

A Ballast 130

Wherein, the ballast 130, as a common electrical control device on lamps, belongs to common knowledge in the art and will no longer be detailed herein. In a preferred implementation, the ballast 130 can regulate the output power of the ultraviolet lamp. In this embodiment, the ballast 130 is connected to the two electrodes 120 and electrifies the two electrodes 120, and after being electrified, the electrodes 120 discharge to the mercury vapor in the discharge cavity 140 to generate ultraviolet light.

Amalgam 150

The amalgam is granular and easier to recycle compared with liquid mercury, and can avoid environmental pollution. FIG. 1 to FIG. 3 further illustrate relevant structures of the amalgam 150, and as shown, the amalgam 150 is stored in a receiving groove 151, which is formed in a first end of the lamp tube 110 and is communicated with the discharge cavity 140, so that the mercury vapor given off by the amalgam 150 can reach the discharge cavity 140.

The first end is preferably an end, formed with the receiving groove 151, of the lamp tube 110 and can be changed according to the actual variation or in different implementations. For example, the first end may be located on the same side as the ballast 130 or may not be located on the same side as the ballast 130. To fulfill a good mercury vapor pressure maintaining effect, the amalgam comprises bismuth, indium, tin and mercury, wherein the proportion of the mercury is 2.0/6-2.5% and can be properly adjusted according to different conditions, and by adoption of different proportions, the amalgam prepared according to the formula of the invention can fulfill a good mercury vapor pressure control effect within a temperature range of 90° C.-135° C., and this temperature range matches the operating temperature of the thermistor 160 in one end socket 152 of the low-pressure and high-intensity ultraviolet lamp.

It should be noted that in a preferred implementation, the receiving groove 151 integrally extends out from one end socket 152, as shown in FIG. 1 to FIG. 3. Specifically, the receiving groove 151 may be a bowl-shaped groove extending from a side, close to the discharge cavity 140, of the end socket 152, and has the amalgam 150 stored therein. This embodiment has no limitation in this aspect. The receiving groove 151 may also be an independent component and is connected to the side, close to the discharge cavity 140, of the end socket 152.

In other preferred implementations, as shown in FIG. 4 to FIG. 9, the receiving groove 151 may be any one of a flat groove 151A, a spherical groove 151B, a tubular groove 151C, a conical groove 151D and an ellipsoidal groove 151E that can store the amalgam 150 and can be communicated with the discharge cavity 140 to allow mercury to circulate between the discharge cavity 140 and the receiving groove 151.

In addition, in a preferred implementation, an opening of the receiving groove 151 is basically upward or tilts upwards in the working state to prevent the amalgam 150 from flowing into the discharge cavity; or, the placement direction of the ultraviolet lamp 100 can be limited, that is, the lamp tube 110 is placed horizontally; or, the receiving groove is placed downwards and the lamp tube tilts upwards; or, the receiving groove is placed downwards, and the lamp tube is placed vertically, so that the amalgam 150 is prevented from leaking from the receiving groove 151.

A Thermistor 160

A significant improvement of the invention against the prior art is that the thermistor 160 is adopted and is integrated with the lamp tube, wherein the thermistor 160 is arranged at the first end of the lamp tube 110, as shown in FIG. 1 and FIG. 2; power receiving terminals C1 and C2 of the thermistor 160 are at least separately connected to one of lead wires a1 and a2 and one of lead wires b1 and b2 of the two electrodes 120. For example, C1 is connected to the lead wire a1 or a2, and C2 is connected to the lead wire b1 or b2. The thermistor 160 is supplied with power by the ballast 130, specifically by a switch power supply of the ballast, so that the number of connecting wires between the lamp tube and the ballast is reduced. In the invention, the two power receiving terminals of the thermistor 160 are preferably connected to lead wires at two terminals of the electrodes, and the voltage of the thermistor 160 is made equal to the voltage of the lamp tube or the sum of the voltage of the lamp tube and the voltage of the electrodes, so that the number of connecting wires between the lamp tube and the ballast can be effectively reduced, the structural characteristics of an existing power supply and the lamp tube can be fully used to arrange the thermistor 160 and integrate the thermistor 160 with the lamp tube, and after being improved, the lamp tube has good structural integrity and can adapt to different ballasts. In addition, the thermistor 160 in this embodiment is preferably a positive temperature coefficient (PTC) thermistor, the resistance of which can increase along with the temperature rise.

In a preferred implementation, the thermistor 160 is packaged in one end socket 152 and contacts with the amalgam 150 in the receiving groove 151 directly or through a heat-conducting material. For example, if the thermistor 160 contacts with the amalgam 150 in the receiving groove 151 directly, the thermistor 160 wraps the receiving groove 151 in a preferred implementation, as shown in FIG. 1 and FIG. 2. In another preferred implementation, as shown in FIG. 3, the thermistor 160 is arranged in one end socket 152 in a sheet shape, extends in the end socket 152, and at least partially warps the receiving groove 151. If the thermistor 160 contacts with the amalgam 150 in the receiving groove 151 through a heat-conducting material, the heat-conducting material is disposed between the thermistor 160 and the receiving groove 151, wherein the heat-conducting material may be a silica gel sheath 170 made of heat-conducting silica gel. On the other hand, the thermistor 160 may be any thermistors with suitable dimensions that are selected by those skilled in the art according to the internal dimension of the lamp tube 110 and are assembled in in the lamp, and details will not be given anymore here. It should noted that the heat-conducting material is arranged for the sake of a better heat-insulation effect, so in this embodiment, the thermistor 160 and the receiving groove 151 are preferably wrapped with the silica gel sheath 170 or other heat-conducting gels in the prior art to keep the thermistor 160 and the receiving groove 151 in tight contact, thus improving the heat conduction effect and stabilizing the temperature of the amalgam 150.

It should be noted that when the temperature of the thermistor is higher than the Curie temperature of the thermistor under the influence of environmental factors, the resistance of the thermistor is large, and the thermistor 160 will hardly generate heat energy. When the temperature of the thermistor is lower than the Curie temperature with the variation of the environmental factors, the thermistor 160 will generate heat after being electrified so as to heat the amalgam 150 to maintain the amalgam 150 at an appropriate temperature, so that the mercury vapor pressure in the discharge cavity 140 is maintained. To match the operating environment of the ultraviolet lamp 100, the parameters of the thermistor 160 need to be limited. The Curie temperature of the thermistor 160 ranges from $[T1+(T2-T1)/5]$ to $[T1+4*(T2-T1)/5]$, wherein T1 and T2 are respectively a minimum operating temperature and a maximum operating temperature of the amalgam 150 in a continuous region where the ultraviolet radiation power is from 90% to 100% when the input power of the ultraviolet lamp is 100%. With the Curie temperature of the thermistor as a critical point, when the temperature of the PTC thermistor is lower than the critical point, the resistance of the thermistor will change very slowly under the influence of the temperature; and when the temperature of the PTC thermistor exceeds the critical point, the resistance of the thermistor will change drastically with the variation of the temperature.

In a preferred implementation, when the ultraviolet radiation power of the ultraviolet lamp is from 90% to 100%, the minimum operating temperature T1 of the amalgam 150 is 90° C., and the maximum operating temperature T2 of the amalgam 150 is 120° C. It can be figured out by calculation according to the above calculation formula that the Curie temperature of the thermistor 160 ranges from 96° C. to 114° C. In other implementations of the invention, the Curie temperature of the thermistor 160 may ranges from 90° C. to 135° C. according to different conditions to adapt to different water temperature environments and wide output power ranges.

To fulfill the above structural improvement, the ultraviolet lamp 100 does not need to be drastically transformed, the cost is low, and little structural space is occupied. By adoption of the above structure, the thermistor 160 can carry out environmental temperature compensation on the amalgam 150. Particularly, when the environmental temperature rises, the temperature of the thermistor 160 will rise, and the resistance will increase, and since the voltage of the lamp tube is stable, in terms of the Ohm's law, in case of the constant voltage, the power will decrease along with the increase of the resistance, heat released by the thermistor 160 is reduced, and the amalgam 150 is heated to a smaller degree. On the contrary, when the environmental temperature drops, the temperature of the thermistor 160 will fall, the resistance of the thermistor 160 will decrease, the power increases, heat released by the thermistor 160 is increased, the amalgam 150 is heated to a greater degree and is finally maintained within a stable temperature range, the mercury vapor pressure in the discharge cavity 140 is indirectly maintained close to the optimal mercury vapor pressure, and high ultraviolet radiation efficiency is ensured.

Furthermore, the ultraviolet lamp 100 further comprises an outer sleeve 180 connected with the lamp tube 110 in a sealed manner. It should be noted that the outer sleeve 180 is preferably an enclosed outer sleeve shown in FIG. 3 and is sealed by the end sockets 152, so that the lamp tube 110 is sealed and accommodated in the outer sleeve 180. Although the outer sleeve 180 is not illustrated in FIG. 1 and FIG. 2, those skilled in the art can obtain corresponding configurations based on an appreciation of this embodiment, and details will no longer be given here. In another preferred implementation, the outer sleeve 180 may be a non-enclosed outer sleeve shown in FIG. 9, and has an opening allowing the lamp tube 110 to enter or come out.

Wherein, the distance between an inner wall of the enclosed or non-enclosed outer sleeve 180 and an outer wall of the lamp tube is preferably from 1.0 mm to 5.0 mm. To prevent the lead wires from moving, the lead wires of the lamp tube should be fixed with rubber rings, and in this case, a 1.00 mm gap is required. If the gap exceeds 5.0 mm, the size of the outer sleeve is large, and the cost is high. The distance from 1.0 mm to 5.0 mm is suitable for the thermal force field distribution of the gap and can adapt to different environmental conditions. The lamp tube 110 and the outer sleeve 180 are both made of quartz pervious to 253.7 nm ultraviolet light or 185 nm and 253.7 nm ultraviolet light. When the lamp tube 110 and the outer sleeve 180 are made of quartz pervious to 253.7 nm ultraviolet light, the ultraviolet lamp can output 253.7 nm ultraviolet light. When the lamp tube 110 and the outer sleeve 180 are made of quartz pervious to 185 nm and 253.7 nm ultraviolet light, the ultraviolet lamp can output 185 nm and 253.7 nm ultraviolet light. At least one of an inert gas and nitrogen is filled between the lamp tube 110 and the outer sleeve 180, and the inert gas or nitrogen is a common gas in the field such as argon, nitrogen, a mixed gas of argon and nitrogen the ratio of which is 5:5, or a mixed gas of argon and neon the ratio of which is 5:5, thus being suitable for sterilization of drinking water, degradation of trace organic substances, and sterilization of household water or indoor water and removal of residual chlorine. The outer sleeve 180 can improve the heat-insulation effect of the mercury vapor in the lamp tube 110, which is beneficial for keeping the mercury vapor pressure stable.

Therefore, based on the above technical solution, those skilled in the art can know that the ultraviolet lamp of the invention has the advantages of good environmental adaptability, wide power regulation range and high ultraviolet radiation efficiency, which are realized by matching the Curie temperature of the thermistor and the operating temperature of the amalgam prepared according to a specific formula.

power regulation in the working area, improves the ultraviolet sterilization efficiency, is suitable for popularization, and has high commercial application value.

To verify the technical effects of the technical solutions of the invention, the inventor carried out the following two contrast tests.

Test 1:

In this test, two ultraviolet lamps were used for water sterilization, wherein one ultraviolet lamp was not provided with a thermistor, which was referred to as Solution A; the other ultraviolet lamp was provided with a thermistor corresponding to the technical solution of the invention, which was referred to as Solution B. The power of lamp tubes of the two ultraviolet lamps was 150 W, the outer diameter of quartz glass tubes was 19 mm, the discharge arc length was 1000 mm, the outer diameter of outer sleeves was 28 mm, the 253.7 nm light transmittance of the quartz glass tubes was 90%, the ultraviolet lamp tubes and the outer sleeves were connected in a sealed manner, the distance between inner walls of the outer sleeves and outer walls of the lamp tubes was 3.0 mm, ballasts with a stable current of 1.5 A were used to drive the ultraviolet lamps to work, the mercury proportion of amalgam was 2.5% of Bi—In—Sn—Hg alloy, and corresponding operating temperatures T1 and T2 within a continuous region of 90%-100% of the ultraviolet radiation power were 90° C. and 120° C. respectively, and the Curie temperature of the thermistor was 100° C. In solution B, the thermistor and the receiving groove 151 were located on the same side of a sealing surface (namely the first end of the lamp tube), heat-conducting silica gel was filled between the thermistor and the receiving groove 151, and the thermistor and the receiving groove 151 were wrapped with a temperature-resistant silicagel sheath. Reference conditions and test results of the two solutions were as follows:

| Solution | Regulation manner of the input power of the lamp | 253.7 nm ultraviolet radiation efficiency when the input power of the lamp is 100% (5° C.-40° C.) | 253.7 nm ultraviolet radiation efficiency when the input power of the lamp is 30% (5° C.-40° C.) | Sterilization efficiency corresponding to 30% of the water flow rate when the input power of the lamp is 30% |
| --- | --- | --- | --- | --- |
| A | Not provided with thermistor | ≥34% | 10%-25% | 50%-98% |
| B | Provided with thermistor | ≥34% | 33%-36% | ≥99.99% |

Although the heating precision of the thermistor 160 to the amalgam 150 is inferior to that of the heating element, the temperature sensor and the control circuit, which may lead to a certain temperature deviation of the amalgam, such as +−5° C., the amalgam 150 prepared according to the specific formula provided by the invention can always maintain the mercury vapor pressure in the lamp close to the optimal mercury vapor pressure within a narrow temperature variation range, thus improving the ultraviolet radiation efficiency of the ultraviolet lamp.

In addition, the thermistor 160 in the invention has a simple power supply circuit and a few lead wires, and the ultraviolet lamp is simple and efficient in overall structure and low in implementation cost, has better performance parameters and better effects, fills in the technical blank in the art, solves the problem of fluctuations of the ultraviolet radiation efficiency of existing low-pressure and high-intensity ultraviolet lamps, can better adapt to the fluctuations of environmental factors such as the temperature, flow rate and Wherein, when the input power of the lamps was 30%, the sterilization efficiency corresponding to 30% of the water flow rate was obtained according to an ultraviolet dose calculated according to biological dose verification data under a typical water temperature of 20° C. and the ultraviolet radiation power of the ultraviolet lamp under a water temperature of 5° C.-40° C. As can be seen, when the input power of the lamp not provided with the thermistor was regulated (Solution A), the temperature of the amalgam was low under a low-power (30%) and low-water temperature (5° C.) condition, the mercury vapor pressure in the lamp was far lower than the optimal mercury vapor pressure, and the ultraviolet radiation efficiency was low. The ultraviolet lamp provided with the thermistor can still maintain high sterilization efficiency in case of large water temperature variation amplitude and wide power range, and a significance improvement effect was realized.

In Test 1, the ultraviolet lamp tube and the outer sleeve in Solution B were both 68% quartz glass tubes with a 253.7 nm light transmittance of 90% and a 185 nm light transmittance of 68%, the ultraviolet lamp tube and the outer sleeve were connected in a sealed manner, a mixed gas of argon and nitrogen at a pressure of 0.8 time of the atmospheric pressure were filled between the lamp tube and the outer sleeve, the ratio of the argon to the nitrogen was 5:5, and the ultraviolet lamp can output 185 nm ultraviolet light and 253.7 nm ultraviolet light to kill microorganisms in water, remove residual chlorine in water and degrade trace organic substances in water.

In Test 1, the ultraviolet lamp in Solution B was driven by a ballast with a stable current of 1.0 A, thus being suitable for sterilizing a air supply system under an environmental temperature of −20° C.-35° C. and an air speed of 2-5 m/s in the breeding industry, and the ultraviolet radiation efficiency of the ultraviolet lamp was not less than 30%.

Test 2:

In this test, two ultraviolet lamps were adopted, wherein one ultraviolet lamp was not provided with a thermistor, which was referred to as Solution C in which a heating temperature-control assembly was adopted; the other ultraviolet lamp was provided with a thermistor corresponding to the technical solution of the invention, which was referred to as Solution D. The power of the two ultraviolet lamp tubes was 250 W, the outer diameter of quartz glass tubes was 19 mm, the discharge arc length was 1470 mm, ballasts with a stable current of 1.8 A were used to drive the ultraviolet lamps to work, the mercury proportion of amalgam was 2.0% of Bi—In—Sn—Hg alloy, and the corresponding operating temperatures T1 and T2 within a continuous region of 90%-100% of the ultraviolet radiation power were 95° C. and 125° C. respectively. Wherein, a set control temperature of the heating temperature-control assembly in Solution C was 105° C.; in Solution D, the thermistor and the receiving groove 151 were located on two sides of a sealing center and were tightly attached to a sealing surface, heat-conducting silica gel was filled between the thermistor and the receiving groove, and the thermistor and the groove formed in the sealing surface were wrapped with a temperature-resistant silica gel sheath. Reference conditions and test results of the two solutions were as follows:

and under different water temperatures and different powers, the ultraviolet lamp had the same ultraviolet radiation efficiency and the same good sterilization efficiency as Solution C. In addition, the outer sleeve in Solution C needed an expanded transition structure, or the diameter of the outer sleeve needed to be increased, so that the cost was increased, and the compatibility with universal equipment was poor. By adoption of the solution of the invention, the structure of the outer sleeve didn't need to be changed, and the compatibility with universal equipment was good.

To sum up, the low-pressure and high-intensity ultraviolet lamp of the invention adopts a PTC thermistor to heat the amalgam to keep it at a constant temperature and has the advantages of good environmental adaptability (temperature and flow rate), wide power regulation range (30%-100% of the rated power), high ultraviolet radiation efficiency and low cost. The thermistor in the low-pressure and high-intensity ultraviolet lamp is supplied with power by a lamp voltage cross two terminals of the electrodes of the ultraviolet lamp, has a simple structure and a few lead wires, and is highly adaptable to ballasts.

It should be noted that the embodiments of the invention can be easily implemented, and are not intended to limit the invention in any form. Any skilled in the art can make alterations or modifications according to the technical contents disclosed above to obtain equivalent embodiments. Any amendments, or equivalent alteration and modifications made to the above embodiments according to the technical principle of the invention without departing from the contents of the technical solutions of the invention should also fall within the scope of the technical solutions of the invention.

What is claimed is:

1. An ultraviolet lamp, comprising a lamp tube and an electrode, a discharge cavity being formed in the lamp tube, wherein a thermistor is disposed on an end socket at a first end of the lamp tube, a receiving groove communicated with the discharge cavity is formed in the end socket, amalgam is stored in the receiving groove, and the thermistor heats the amalgam in the receiving groove in the end socket, further comprising an outer sleeve disposed around the lamp tube

| Solution | Regulation manner of the input power of the lamp | 253.7 nm ultraviolet radiation efficiency when the input power of the lamp is 100% (5° C.-40° C.) | 253.7 nm ultraviolet radiation efficiency when the input power of the lamp is 30% (5° C.-40° C.) | Length dimension of lamp holder | Sterilization efficiency corresponding to 30% of the water flow rate when the input power of the lamp is 30% |
|---|---|---|---|---|---|
| C | Heating temperature-control assembly | ≥34% | 33%-36% | outer diameter 28 mm × length 60 mm | ≥99.99% |
| D | Thermistor | ≥34% | 33%-36% | outer diameter 23 mm × length 35 mm | ≥99.99% |

Wherein, when the input power of the lamp is 30%, the sterilization efficiency corresponding to 30% of the water flow rate was obtained according to an ultraviolet dose calculated according to biological dose verification data under a typical water temperature of 20° C. and the ultraviolet radiation power of the ultraviolet lamp under a water temperature of 5° C.-40° C. As can be seen, compared with Solution C, the heating temperature-control assembly in the solution of the invention was simple, the lamp holder had a small outer diameter and a small length and was low in cost and didn't need a special ballast like a common lamp holder, and spaced from the lamp tube, wherein a distance between an inner wall of the outer sleeve and an outer wall of the lamp tube is 1.0 mm-5.0 mm, the lamp tube and the outer sleeve are connected in a sealed manner, at least one of an inert gas and nitrogen is filled between the lamp tube and the outer sleeve, both the lamp tube and the outer sleeve are made of quartz pervious to 185 nm and 253.7 nm ultraviolet light, and the lamp tube and the outer sleeve are integrated and are able to output the 185 nm and 253.7 nm ultraviolet light, wherein at least one terminal of a thermistor lead wire is connected to one terminal of electrode lead wires, wherein the Curie temperature of the thermistor ranges from [T1+(T2−T1)/5] to [T1+4*(T2−T1)/5], wherein T1 and T2 are respectively a minimum operating temperature and a maximum operating temperature of the amalgam in a continuous region where the ultraviolet radiation power is from 90% to 100% when the input power of the ultraviolet lamp is 100%, wherein the amalgam comprises bismuth, indium, tin and mercury, and the proportion of the mercury is 2.0%-2.5%.

2. The ultraviolet lamp according to claim 1, wherein the receiving groove is at east one of a flat groove, an ellipsoidal groove, a conical groove, a spherical groove and a tubular groove.

3. The ultraviolet lamp according to claim 1, wherein the Curie temperature of the thermistor ranges from 90° C. to 35'C, and a current density of the ultraviolet lamp is greater than 0.13 ampere per square centimeter.

4. The ultraviolet lamp according to claim 1, wherein the thermistor and the receiving groove are wrapped with at least one of heat-conducting silica gel and a silica gel sheath.

5. The ultraviolet lamp according to claim 1, wherein the receiving groove contacts with the thermistor directly, or indirectly through a heat-conducting material.

6. The ultraviolet lamp according to claim 1, the outer sleeve disposed around the lamp tube and spaced from the lamp tube, wherein a distance between an inner wall of the outer sleeve and an outer wall of the lamp tube is 1.0 mm-5.0 mm, and the lamp tube and the outer sleeve are connected in a non-sealed manner.

* * * * *

UNITED STATES PATENT AND TRADEMARK OFFICE
CERTIFICATE OF CORRECTION

PATENT NO. : 11,318,222 B2  
APPLICATION NO. : 17/263641  
DATED : May 3, 2022  
INVENTOR(S) : Zhiming He Page 1 of 1

It is certified that error appears in the above-identified patent and that said Letters Patent is hereby corrected as shown below:

In the Claims

Column 13, Lines 9-10, Claim 2:  
After "wherein the receiving groove is at"  
Delete "east"  
Insert --least--.

Signed and Sealed this  
Tenth Day of September, 2024

Katherine Kelly Vidal  
*Director of the United States Patent and Trademark Office*